US007972773B2

(12) United States Patent
Madonna et al.

(10) Patent No.: US 7,972,773 B2
(45) Date of Patent: *Jul. 5, 2011

(54) METHOD FOR DETECTING CONCENTRATIONS OF A TARGET BACTERIUM THAT USES PHAGES TO INFECT TARGET BACTERIAL CELLS

(75) Inventors: Angelo J. Madonna, Tooele, UT (US); Kent J. Voorhees, Golden, CO (US); Jon C. Rees, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/626,326

(22) Filed: Jan. 23, 2007

(65) Prior Publication Data
US 2007/0275370 A1    Nov. 29, 2007

Related U.S. Application Data

(63) Continuation of application No. 10/249,452, filed on Apr. 10, 2003, now Pat. No. 7,166,425.

(60) Provisional application No. 60/319,184, filed on Apr. 12, 2002.

(51) Int. Cl.
*C12Q 1/02* (2006.01)
*C12Q 1/04* (2006.01)
*C12Q 1/70* (2006.01)
*G01N 33/53* (2006.01)
*A01N 63/00* (2006.01)

(52) U.S. Cl. .......... 435/5; 435/4; 435/7.1; 435/7.2; 435/7.32; 435/7.5; 424/93.1; 424/93.3; 424/93.6

(58) Field of Classification Search .................. None
See application file for complete search history.

(56) References Cited

U.S. PATENT DOCUMENTS

| | | | |
|---|---|---|---|
| 3,839,175 A | 10/1974 | Keyes | |
| 4,104,126 A | 8/1978 | Young | |
| 4,764,473 A | 8/1988 | Matschke | |
| 4,797,363 A | 1/1989 | Teodorescu et al. | |
| 4,861,709 A | 8/1989 | Ulitzur et al. | |
| 5,085,982 A | 2/1992 | Keith | |
| 5,101,105 A | 3/1992 | Fenselau et al. | |
| 5,126,024 A | 6/1992 | Bonelli et al. | |
| 5,135,870 A | 8/1992 | Williams et al. | |
| 5,168,037 A | 12/1992 | Entis et al. | |
| 5,443,987 A | 8/1995 | Decicco et al. | |
| 5,445,942 A | 8/1995 | Rabin et al. | |
| 5,469,369 A | 11/1995 | Rose-Pehrsson et al. | |
| 5,476,768 A | 12/1995 | Pearson et al. | |
| 5,498,525 A | 3/1996 | Rees et al. | |
| 5,498,528 A | 3/1996 | King | |
| 5,550,062 A | 8/1996 | Wohltjen et al. | |
| 5,620,845 A * | 4/1997 | Gould et al. | 435/5 |
| 5,656,424 A | 8/1997 | Jurgensen et al. | |
| 5,658,747 A | 8/1997 | Feldsine et al. | |
| 5,679,510 A | 10/1997 | Ray et al. | |
| 5,710,005 A | 1/1998 | Rittenburg | |
| 5,723,330 A | 3/1998 | Rees et al. | |
| 5,766,840 A | 6/1998 | Kim et al. | |
| 5,789,174 A | 8/1998 | Mouton et al. | |
| 5,824,468 A | 10/1998 | Scherer et al. | |
| 5,859,375 A | 1/1999 | Danylewych-May et al. | |
| 5,874,226 A | 2/1999 | Zeytinoglu et al. | |
| 5,888,725 A | 3/1999 | Sanders | |
| 5,914,240 A | 6/1999 | Sanders | |
| 5,958,675 A | 9/1999 | Wicks et al. | |
| 5,985,596 A | 11/1999 | Wilson | |
| 6,004,770 A | 12/1999 | Nelson | |
| 6,037,118 A | 3/2000 | Thomas et al. | |
| 6,090,541 A | 7/2000 | Wicks et al. | |
| 6,093,541 A | 7/2000 | Nelson | |
| 6,177,266 B1 | 1/2001 | Krishnamurthy et al. | |
| 6,183,950 B1 | 2/2001 | Voorhees et al. | |
| 6,235,480 B1 | 5/2001 | Shultz et al. | |
| 6,265,169 B1 | 7/2001 | Cortese et al. | |

(Continued)

FOREIGN PATENT DOCUMENTS
DE        43 14998    * 11/1994
(Continued)

OTHER PUBLICATIONS

Chatterjee et al., "A high yielding mutant of mycobacteriophage L1 and its application as a diagnostic tool," FEMS Microbiology Letters, vol. 188 No. 1, pp. 47-53 (Jul. 2000).*
Stewart et al., "The specific and sensitive detection of bacterial pathogens within 4 h using bacteriophage amplification," Journal of applied microbiology, vol. 84 No. 5, pp. 777-783 (May 1998).*
U.S. Appl. No. 60/418,822, filed Oct. 15, 2002, Anderson et al.
International Search Report, PCT/US03/11253, WO 03/087772A2 & A3 Feb. 28, 2005, [187280/PCT].
European Supplemental Search Report, EP/03726259, Apr. 6, 2006 [187280/EP].

(Continued)

Primary Examiner — Zachariah Lucas
Assistant Examiner — Nicole Kinsey White
(74) Attorney, Agent, or Firm — Dorsey & Whitney LLP (57) ABSTRACT

The invention is directed to a method for detecting low concentrations of bacteria in liquid solution that may or may not be complex liquid solutions. In one embodiment, immunomagnetic separation (IMS) is used to separate target bacterium that may be in a liquid mixture from other constituents in the mixture. A low concentration of a bacteriophage for the target bacteria is subsequently used to infect target bacterial cells that have been captured using the IMS technique. If at least a certain concentration of target bacterium are present, the bacteriophage will multiply to a point that is detectable. Matrix assisted laser desorption ionization/time-of-flight-mass spectrometry (MALDI/TOF-MS) is then used to produce a mass spectrum that is analyzed to determine if one or more proteins associated with the bacteriophage are present, thereby indirectly indicating that target bacterium were present in the liquid mixture.

4 Claims, 5 Drawing Sheets

U.S. PATENT DOCUMENTS

| | | | |
|---|---|---|---|
| 6,300,061 | B1 | 10/2001 | Jacobs, Jr. et al. |
| 6,316,266 | B1 | 11/2001 | Nelson |
| 6,322,783 | B1 | 11/2001 | Takahashi |
| 6,355,445 | B2 | 3/2002 | Cherwonogrodzky et al. |
| 6,428,976 | B1 | 8/2002 | Chang et al. |
| 6,436,652 | B1 | 8/2002 | Cherwonogrodzky et al. |
| 6,436,661 | B1 | 8/2002 | Adams et al. |
| 6,461,833 | B1 | 10/2002 | Wilson |
| 6,514,767 | B1 | 2/2003 | Natan |
| 6,514,778 | B2 | 2/2003 | Huang |
| 6,524,809 | B1 | 2/2003 | Wilson |
| 6,544,729 | B2 | 4/2003 | Sayler et al. |
| 6,555,312 | B1 | 4/2003 | Nakayama |
| 6,580,068 | B1 | 6/2003 | Tarver et al. |
| 6,660,437 | B2 | 12/2003 | Friedrich et al. |
| 6,660,470 | B1 | 12/2003 | Sanders |
| 6,787,360 | B2 | 9/2004 | Agrawal et al. |
| 6,799,119 | B1 | 9/2004 | Voorhees et al. |
| 6,824,975 | B2 | 11/2004 | Hubscher et al. |
| 6,913,753 | B2 | 7/2005 | Ramachandran |
| 7,034,113 | B2 | 4/2006 | Olstein |
| 7,087,376 | B2 | 8/2006 | Miller |
| 7,166,425 | B2 * | 1/2007 | Madonna et al. .................. 435/5 |
| 7,195,778 | B2 | 3/2007 | Flashner-Barak et al. |
| 2002/0192676 | A1 | 12/2002 | Madonna et al. |
| 2003/0175207 | A1 | 9/2003 | Olstein et al. |
| 2004/0002126 | A1 | 1/2004 | Houde et al. |
| 2004/0121403 | A1 | 6/2004 | Miller |
| 2004/0137430 | A1 | 7/2004 | Anderson et al. |
| 2005/0003346 | A1 | 1/2005 | Voorhees et al. |
| 2005/0208475 | A1 | 9/2005 | Best et al. |
| 2005/0250096 | A1 | 11/2005 | Wheeler et al. |
| 2005/0255043 | A1 | 11/2005 | Hnatowich et al. |
| 2007/0059725 | A1 | 3/2007 | Voorhees |
| 2007/0148638 | A1 | 6/2007 | Madonna et al. |
| 2007/0178450 | A1 | 8/2007 | Wheeler et al. |
| 2007/0249012 | A1 | 10/2007 | Lye et al. |
| 2009/0208996 | A1 | 8/2009 | Kadurugamuwa et al. |
| 2009/0246752 | A1 | 10/2009 | Voorhees et al. |
| 2009/0246753 | A1 | 10/2009 | Voorhees |
| 2009/0258341 | A1 | 10/2009 | Voorhees et al. |
| 2009/0286225 | A1 | 11/2009 | Voorhees et al. |
| 2009/0286232 | A1 | 11/2009 | Voorhees et al. |

FOREIGN PATENT DOCUMENTS

| | | |
|---|---|---|
| EP | 0168933 | 2/1986 |
| EP | 0228975 * | 7/1987 |
| EP | 0439354 A2 | 7/1991 |
| EP | 1300082 A2 | 4/2003 |
| WO | WO 85/04189 | 9/1985 |
| WO | WO 88/04326 | 6/1988 |
| WO | WO 92/02633 * | 2/1992 |
| WO | WO 93/11161 | 6/1993 |
| WO | WO 93/17129 A1 | 9/1993 |
| WO | WO 94/06931 | 3/1994 |
| WO | WO 94/13804 | 6/1994 |
| WO | WO 95/05483 A1 | 2/1995 |
| WO | WO 98/08944 | 3/1998 |
| WO | WO 98/18962 A1 | 5/1998 |
| WO | WO 00/10013 | 2/2000 |
| WO | WO 01/25395 | 4/2001 |
| WO | WO 02/06117 A1 | 8/2002 |
| WO | WO 03/035889 A2 | 5/2003 |
| WO | WO 03/087772 A2 | 10/2003 |
| WO | WO 03/087772 A3 | 10/2003 |
| WO | WO 2006/012371 | 2/2006 |
| WO | WO 2006/083292 | 8/2006 |
| WO | WO 2006/105504 | 10/2006 |
| WO | WO 2008/064241 | 5/2008 |

OTHER PUBLICATIONS

Abbas-Hawks et al., "In Situ Methylation of Nucleic Acids Using Pyrolysis/Mass Spectrometry," Rapid Communications in Mass Spectrometry, vol. 10, pp. 1802-1806, 1996.

Barringer Research Limited, "Biological Agent Detection by Ion Mobility Spectrometery (Final Report)," CR96-012, pp. 1-25, Apr. 1996.

Basile et al., "Pathogenic Bacteria: Their Detection and Differentiation by Rapid Lipid Profiling with Pyrolysis Mass Spectrometry," Tends in Analytical Chemistry, vol. 00, No. 0, pp. 1-15, 1997, Elsevier Science B.V., The Netherlands.

Basile et al., "Direct Mass Spectrometric Analysis of in Situ Termally Hydrolyzed and Methylated Lipids from Whole Bacterial Cells," submitted to Analytical Chemistry, 34 pages, at least as early as Apr. 12, 2002.

Beverly et al., "A Rapid Approach for the Detection of Dipicolinic Acid in Bacterial Spores Using Pyrolysis/Mass Spectrometry," Rapid Communications in Mass Spectrometry, vol. 10, pp. 455-458, 1996.

Bordner et al., "Microbiological Methods For Monitoring the Environment—Water and Wastes," Dec. 1978, prepared in part under EPA Contract No. 68-03-0431, Environmental Monitoring and Support Laboratory, Office Of Research and Development, USEPA, pp. i-xvi, 1-338, Cincinnati, Ohio.

Brockman et al., "Probe-Immobilized Affinity Chromatography/Mass Spectrometry", Analytical Chemistry, vol. 67, No. 24, pp. 4581-4585, Dec. 15, 1995, American Chemical Society, USA.

Bundy et al., "Lectin and Carbohydrate Affinity Caputre Surfaces for Mass Spectrometric Analysis of Microorganisms", Analytical Chemistry, vol. 73, No. 4, pp. 751-575, Feb. 15, 2001, American Chemical Society, USA.

Cluett et al., "The Envelope of Vaccinia Virus Reveals an Unusual Phospholipid in Golgi Complex Membranes," Journal of Cell Science, 109, pp. 2121-2131, 1996, Great Britain.

Crews et al., "Lipids Are Major Components of Human Immunodeficiency Virus: Modification of HIV Lipid Composistion, Membrane Organization, and Protein Conformation by AL-721," Drug Development Research 14:31-44, 1988.

Cudjoe et al., "Immunomagnetic Separation of *Salmonella* from Foods and Their Detection Using Immunomagnetic Particle (IMP)-ELISA," International Journal of Food Microbiology, Sep. 1995, pp. 11-25, vol. 27, No. 1, Elsevier Science, The Netherlands.

Deluca et al., Pyrolysis-Mass Spectrometry Methodology Applied to Southeasst Asian Environmental Samples for Differentiating Digested and Undigested Pollens, Analytical Chemistry, vol. 58, 2439-2442, 1986.

Deluca et al., "Direct Analysis of Bacterial Fatty Acids by Curie-Point Pyrolysis Tandem Mass Spectrometry," Analytical Chemical Society, vol. 62, No. 14, pp. 1465-1472, 1990.

Deluca et al., "Direct Analysis of Bacterial Glycerides by Curie-Point Pyrolysis-Mass Spectrometry," Journal of Analytical and Applied Pyrolysis, vol. 23, pp. 1-14, 1992, Elsevier Science Publishers B.V., The Netherlands.

Dickinson et al., "New and Improved Strategies for the Rapid Detection and Differential Identification of Microbial Spores Using MALDI-TOFMS," Proceedings of the 50th ASMS Conference on Mass Spectrometry and Allied Topics, Orlando, Florida, 2 pages; Jun. 2-6, 2002.

Dubow, "Bacterial Identification—Use of Phages," section in Encyclopedia Virology, 2nd Edition, R.G. Webster and A. Granoff (eds.), pp. 137-139, 1999, Academic Press, San Diego, California.

Dziadkowiec et al., "The Detection of *Salmonella* in Skimmed Milk Powder Enrichments Using Conventional Methods and Immunomagnetic Separation," Letters in Applied Microbiology, 1995, pp. 361-364, vol. 20, The Society for Applied Bacteriology, Blackwell Science, UK.

Ember, "Chemical Warfare Agent Detectors Probe the Fogs of War," C&EN, pp. 26-32, Aug. 1, 1994.

Favrin et al., "Development and Optimization of a Novel Immunomagnetic Separation-Bacteriophage Assay for Detection of *Salmonella enterica* Serovar Enteritidis in Broth," Applied and Environmental Microbiology, Jan. 2001, pp. 217-224, vol. 67, No. 1, American Society for Microbiology, Washington, D.C.

Franz, et al., "Clinical Recognition and Management of Patients Exposed to Biological Warfare Agents," JAMA, vol. 278, No. 5, pp. 399-411, Aug. 6, 1997, USA.

Gantt et al., "Use of an Internal Control for Matrix-Assisted Laser Desorption/Ionization Time-of-Flight Mass Spectrometry Analysis of Bacteria", J Am Soc Mass Spectrom, 1999, pp. 1131-1137, vol. 10, American Society for Mass Spectrometry, Elsevier Science, The Netherlands.

Gharaibeh et al., : Characterization of Lipid Fatty Acids in Whole-Cell Microorganisms Using in Situ Supercritical Fluid Derivatization/Extraction and Gas Chromatography/Mass Spectrometry, Analytical Chemistry, vol. 68, pp. 2805-2810, 1996.

Girault et al., "Coupling of MALDI-TOF Mass Analysis to the Separation of Biotinylated Peptides by Magnetic Streptavidin Beads," Analytical Chemistry, vol. 68, No. 13, pp. 2122-2126, Jul. 1, 1996, American Chemical Society, USA.

Goodacre et al., "Rapid Identification Using Pyrolysis Mass Spectrometry and Artificial Neural Networks of *Propionibacterium Acnes* Isolated from Dogs," Journal of Applied Bacteriology, vol. 76, pp. 124-134, 1994.

Grant et al., "Isolation of *Mycobacaterium paratuberculosis* from Milk by Immunomagnetic Separation," *Applied and Environmental Microbiology*, vol. 64, No. 9, pp. 3153-3158, Sep. 1998, American Society for Microbiology, USA.

Gross et al., "Mass Spectral Studies of Probe Pyrolysis Products of Intact Oligoribonucleotides," Nucleic Acids Research, vol. 5, No. 8, pp. 2695-2704, Aug. 1978, Department of Chemistry, University of Nebraska, Lincoln, Nebraska.

Hahner et al., "Matrix-Assisted Laser Desorption/Ionization Mass Spectrometry (MALDI) of Endonuclease Digests of RHA," Nucleic Acids Research, vol. 25, No. 10, pp. 1957-1964, 1997, Oxford University Press, UK.

Hendricker, "An Investigation into the Curie-point Pyrolysis-Mass Spectrometry of Glycyl Dipeptides," Journal of Analytical and Applied Pyrolysis, vol. 36, pp. 51-70, 1996.

Heylin, "The Chemicals of War," 1 page, C&EN, Mar. 9, 1998.

Higgins et al., "Competitive Oligonucleotide Single-Base Extension Combined with Mass Spectrometric Detection for Mutation Screening," BioTechniques, vol. 23, No. 4, pp. 710-714, Oct. 1997, Eaton Publishing Co., USA.

Hirsch, et al., "Rapid Detection of *Salmonella* spp. By Using Felix-O1 Bacteriophage and High-Performance Liquid Chromatography," Applied and Environmental Microbiology, vol. 45, No. 1, pp. 260-264, Jan. 1993, American Society for Microbiology, Washington, D.C.

Holland et al.,"Rapid Identification of Intact Whole Bacteria Based on Spectral Patterns Using Matrix-Assisted Laser Desorption/Ionization with Time-of-Flight Massd Spectrometry," Rapid Communications In Mass Spectrometry, vol. 10, pp. 1227-1232, 1996.

Holmes et al., "Coronaviridae: The Viruses and Their Replication," Fundamental Virology, Third Edition, B.N. Fields et al. (eds.), pp. 541-559, 1996, Lippincott-Raven Publishers, Philadelphia.

Huang et al., "Interplay Between Lipids and Viral Glycoproteins During Hemolysis and Fusion by Influenza Virus," The Journal of Biological Chemistry, vol. 261, No. 28, pp. 12911-12914, 1986.

Jenison et al., "Silicon-Based Biosensors for Rapid Detection of Protein or Nucleic Acid Targets," Clinical Chemistry, vol. 47, No. 10, pp. 1894-1900, Oct. 2001, American Association for Clinical Chemistry, Inc.

Jenison et al., "Thin Film Biosensor for Rapid Detection of mecA from Methicillin-resistant *Staphylococcus aureus*,"Clinical Chemistry, vol. 46, No. 9, pp. 1501-1504, Sep. 2000, American Association for Clinical Chemistry, Inc.

Kermasha et al., "Comparative High-Performance Liquid Chromatographic Analyses of Cholesterol and Its Oxidation Products Using Diode-Array Ultraviolet and Laser Light-Scattering Detection," Journal of Chromatography A, vol. 685, pp. 229-235, 1994.

Kingsbury et al, "Rapid Detection and Identification of Infectious Agents," pp. i-xii, 1-296, Academic Press, Inc., Orlando, Florida 1985.

Kodikara et al., "Near On-Line Detection of Enteric Bacteria Using Lux Recombinant Bacteriophage," FEMS Microbiology Letter, vol. 83, pp. 261-265, 1991, Federation of European Microbiological Societies, Elsevier, The Netherlands.

Lamoureux et al., "Detection of *Campylobacter jejuni* in Food and Poultry Viscera Using Immunomagnetic Separation and Microtitre Hybridization", Journal of Applied Microbiology, vol. 83, pp. 641-651, 1997, The Society for Applied Bacateriology, UK.

Le Cacheux et al., "Quantitative Analysis of Cholesterol and Cholesterol Ester Mixtures Using Near-Infared Fourier Transform Raman Spectroscopy," Applied Spectroscopy, vol. 50, No. 10, pp. 1253-1257, 1996.

Lynn et al., "Identification of Enterobacteriaceae Bacteria by Direct Matrix-assisted Laser Desorption/Ionization Mass Spectrometric Analysis of Whole Cells," vol. 13, No. 20, pp. 2022-2027, 1999, John Wiley & Sons, Ltd., Hoboken USA.

Madonna et al., "Detection of Bacteria from Biological Mixtures Using Immunomagnetic Separation Combined with Matrix-Assisted Laser Desorption/Ionization Time-of-Flight Mass Spectrometry," Rapid Communications in Mass Spectrometry, vol. 15, No. 13, pp. 1068-1074, Jun. 6, 2001, John Wiley & Sons, Ltd., Hoboken, USA.

Madonna et al., "Detection of *Escherichia coli* Using Immunomagnetic Separation and Bacteriophage Amplification Coupled with Matrix-assisted laser Desorption/Ionization Time-of-flight Mass Spectrometry," Rapid communications in Mass Spectrometry, published online Dec. 24, 2002 in Wiley InterScience (www.interscience.wiley.com), pp. 257-263, vol. 17, John Wiley & Sons, Ltd.

Madonna et al., "Isolation and Enrichment of *Salmonella* on Immunomagnetic Beads Prior to Detection by MALDI-TOFMS" (extended abstract), *49th ASMS Conference on Mass Spectrometry and Allied Topics*, May 27-31, 2001, Session Code: MPI, Slot: 204, 1 page, USA.

Madonna et al., "Investigation of Cell Culture Media Infected with Viruses by Pyrolysis Mass Spectrometry: Implications for Bioaerosol Detection," American Society for Mass Spectrometry, vol. 10, No. 6, pp. 502-511 Jun. 1999.

Madonna, et al., "Investigation of Viruses Using Pyrolysis Mass Spectrometry," [appears to be an internal power point presentation].

Mansfield et al., "Immunomagnetic Separation as an Alternative to Enrichmnet Broths for *Salmonella* Detection", Letters in Applied Microbiology, vol. 16, pp. 122-125, 1993.

Marple et al., "Aerosol Sample Acquisition for Chemical and Biological Agent Detection," Abstract, Report No. ARO-25616.1-CHS, Army Research Office, Dec. 1, 1989.

Meuzelaar et al., "Characterization of Leukemic and Normal White Blood Cells by Curie-Point Pyrolysis-Mass Spectrometry. Biochemical Interpretation of Some of the Differences in the Pyrolysis Patterns," Journal of Analytical and Applied Pyrolysis, vol. 3, pp. 111-129, 1981.

Munoz-Barroso et al., "Dynamic Properties of Newcastle Disease Virus Envelope and Their Relations with Viral Hemagglutinin-Neuraminidase Membrane Glycoprotein," Biochimica et Biophysica Acta, vol. 1327, pp. 17-31, 1997.

Nakamura et al., "A Visualizatoin Method of Filamentous Phage Infection and Phage-Derived Proteins in *Escherichia coli* Using Biotinylated Phages," Biophysical and Biophysical Research Communications, vol. 289, No. 1, pp. 252-256 Nov. 2001.

Nelson et al., "Mass Spectrometric Immunoassay", Analytical Chemistry, vol. 67, No. 7, pp. 1153-1158, Apr. 1, 1995, American Chemical Society, USA.

Nyiendo, et al., "Preparation and Storage of High-Titer Lactic Streptococcus Bacteriophages," Applied Microbioilogy, vol. 27, No. 1, pp. 72-77, Jan. 1974, American Society for Microbiology.

Okrend et al., "Isolation of *Escherichia coli* O157:H7 Using O157 Specific Antibody Coated Magnetic Beads",*Journal of Food Protection*, Mar. 1992, pp. 214-217, 55, International Association of Milk, Food and Environmental Sanitarians.

Olsvik et al., "Magnetic Separation Techniques in Diagnostic Microbiology," Clinical Microbiology Reviews, vol. 7 No. 1, pp. 43-54, Jan. 1994.

Ostlund et al., "Quantification of Cholesterol Tracers by Gas Chromotography-Negative Ion Chemical Ionization Mass Spectrometry," Journal of Mass Spectrometry, 31:1291-1296, 1996.

Patzer et al., "Lipid Organization of the Membrane of Vesicular Stomatitis Virus," The Journal of Biological Chemistry, vol. 253, No. 13, pp. 4544-4550, Jul. 1978.

Pugh et al., "A Complete Protocol Using Conductance for Rapid Detection of *Salmonellas* in Confectionary Materials," Letters in Applied Microbiology, 1988, p. 23-27, vol. 7, The Society for Applied Microbiology, Blackwell Science, UK.

Pyle et al., "Sensitive Detection of *Escherichia coli* O157:H7 in Food and Water by Immunomagnetic Separation and Solid-Phase Laser Cytometry", Applied and Environmental Microbiology, May 1999, pp. 1966-1972, vol. 65, No. 5, American Society for Microbiology, Washington, D.C.

Rowe et al., "An Array Immunosensor for Simultaneous Detection of Clinical Analytes", *Analytical Chemistry*, Jan. 15, 1999, 71-#2, American Chemical Society, USA.

Ryzhov et al., "Characterization of the Protein Subset Desorbed by MALDI from Whole Bacterial Cells," Analytical Chemistry, Feb. 15, 2001, pp. 746-750, vol. 73, No. 4, American Chemical Society, Washington, D.C.

Sanderson, et al., "Surface Sampling Methods for *Bacillus anthracis* Spore Contamination," Emerging Infectious Diseases, vol. 8, No. 10, pp. 1145-1151, Oct. 2002.

Schlesinger, "Detecting Battlefield Toxins," Popular Science, 2 pages Oct. 1998.

Siuzdak, "Probing Viruses with Mass Spectrometry," *Journal of Mass Spectrometry*, vol. 33, pp. 203-211, 1998, John Wiley & Sons Ltd.

Skjerve et al., "Detection of *Listeria Monocytogenes* in Foods by Immunomagnetic Separation," Applied and Environmental Microbiology, Nov. 1990, pp. 3478-3481, vol. 56, No. 11, American Society for Microbiology, Washington, DC.

Stankiewicz et al., "Assessment of Bog-body Tissue Preservation by Pyrolysis-Gas Chromatography/Mass Spectrometry," Rapid Communications in Mass Spectrometry, vol. 11, pp. 1884-1890, 1997.

Stewart, "In vivo bioluminescence: new potentials for microbiology," Letters in Applied Microbiology, vol. 10, pp. 1-8, 1990, The Society for Applied Microbiology, Blackwell Science, UK.

Strauss, et al., "Purification and Properties of Bacteriophage MS2 and of its Ribonucleic Acid," J. Mol. Biol., vol. 7, pp. 43-54, 1963, Elsevier Science, The Netherlands.

Sun et al., Use of Bioluminescent *Salmonella* for Assessing the Efficiency of Constructed Phage-Based Biosorbent, *Journal of Industrial Microbiology & Biotechnology*, 2000, vol. 25, pp. 273-275, Nature Publishing Group.

Sun et al., "Use of Bioluminescent *Salmonella* for Assessing the Efficiency of Constructed Phage-Based Biosorbent," Journal of Industrial Microbiology & Biotechnology, vol. 27, No. 2, pp. 126-128, Aug. 2001.

Tan et al., "Rapid Simultaneous Detection of Two Orchid Viruses Using LC- and/or MALDI-mass Spectrometry," *Journal of Virological Methods*, vol. 85, pp. 93-99, 2000, Elsevier Science B.V., The Netherlands.

Tas et al., "Characterization of Virus Infected Cell Cultures by Pyrolysis/Direct Chemical Ionization Mass Spectrometry," Biomedical and Environmental Mass Spectrometry, vol. 18, pp. 757-760, 1989.

Thomas et al., "Viral Characterization by Direct Analysis of Capsid Proteins," Analytical Chemistry, vol. 70, No. 18, pp. 3863-3867, Sep. 15, 1998.

Tremblay, "DARPA Expands R&D on Biowarfare Defense Tools," 1 page, C&EN, Feb. 16, 1998.

Van Der Wolf et al., "Immunomagnetic separation of *Erwinia caratovora* subsp. Astroseptica from potato peel extracts to improve detection sensitivity on a crystal violet pectate medium or by PCR," Journal of Applied Bacteriology, vol. 80, pp. 487-495, May 1996, Blackwell Science, UK.

Van Hoeven et al., "Studies on Plasma Membranes," Biochimica et Biophysica Acta, vol. 380, pp. 1-11, 1975, Elesevier Scientific Publication Company, The Netherlands.

Voorhees et al., "An Investigation of the Pyrolysis of Oligopeptides by Curie-point Pyrolysis-tandem Mass Spectrometry," Journal of Analytical and Applied Pyrolysis, vol. 30, pp. 1-16, 1994, Elsevier Science B.V., The Netherlands.

Wang et al., "Investigation of Spectral Reproducibility in Direct Analysis of Bacteria Proteins by Matrix-Assisted Laser Desorption/Ionization Time-of-Fight Mass Spectrometry," Rapid Communications in Mass Spectrometry, vol. 12, pp. 456-464, 1998, John Wiley & Sons, Ltd., Hoboken, USA.

Windig et al., "Control of the Absence of Deae-Polysaccharides in Deae-Sephadex Purified Poliovirus Suspensions by Pryolysis Mass Spectrometry," Develop. Biol Standard, vol. 47, pp. 169-177, 1981.

Wyatt et al., "Immunoassays for Food-poisoning Bacteria and Bacterial Toxins," Nov. 1992, pp. i-xiii, 1-129, James & James (Science Publishers) Ltd. and Chapman & Hall, London, Great Britain.

Yates et al., "Method to Compare Collison-Induced Dissociation Spectra of Peptides: Potential for Library Searching and Subtractive Analysis," Analytical Chemisry, vol. 70, pp. 3557-3565, 1998.

Yu et al, "Immunomagnetic-Electrochemiluminescent Detection of *Escherichia coli* O157 and *Salmonella typhimurium* in Foods and Environmental Water Samples," Applied and Environmental Microbiology, vol. 62, No. 2, pp. 587-592, Feb. 1996, American Society for Microbiology, Washington, D.C.

Bird et al., "Single-Chain Antigen-Binding Proteins," *Science*, 1988, vol. 242, pp. 423-426.

Carter, "Potent antibody therapeutics by design," *Nature Reviews Immunology*, 2006, vol. 6, pp. 343-357.

Casini et al., "In vitro papillomavirus capsid assembly analyzed by light scattering," *Virology*, 2004, vol. 325, pp. 320-327.

Garcia, et al., "The Genome Sequence of *Yersinia pestis* Bacteriophage ΦA1122 Reveals an Intimate History with the Coliphage T3 and T7 Genomes," *Journal of Bacteriology*, Sep. 2003, vol. 185, No. 17, pp. 5248-5262.

Haynes et al., "Surface Enhanced Raman Spectroscopy," *Anal. Chem.*, 2005, pp. 339A-346A.

Holliger et al., "Diabodies: Small bivalent and bispecific antibody fragments," *Proc. Natl. Acad. Sci. U.S.A.*, 1993, vol. 90, pp. 6444-6448.

Holliger et al., "Engineered antibody fragments and the rise of single domains," *Nature Biotechnology*, 2005, vol. 23, No. 9, pp. 1126-1136.

Huston et al., "Protein engineering of antibody binding sites: Recovery of specific activity in an anti-digoxin single-chain Fv analogue produced in *Escherichia coli,*" *Proc. Natl. Acad. Sci.* U.S.A, 1988, vol. 85, pp. 5879-5883.

Lech, et al., "Section III Vectors Derived from Lambda and Related Bacteriophages," Current Protocols in Molecular Biology, Frederick M. Ausubel, et al. (Editor), ISBN: 978-0-471-50338-5, 1987, 34 pages.

Madonna, et al., "On-probe sample pretreatment for the detection of proteins above 15 Kda from whole cell bacteria by matrix-assisted laser desorption/ionization time-of-flight mass spectrometry," *Rapid Communications in Mass Spectrometry*, 2000, vol. 14, p. 2220-2229.

Sambrook et al., Molecular Cloning: A Laboratory Manual, Second Edition, 1889, Cold Spring Harbor Laboratory Press, 27 pages (Title page and Table of Contents).

Tomlinson et al., "Methods for Generating Multivalent and Bispecific Antibody Fragments," *Methods Enzymol.*, 2000, vol. 326, pp. 461-479.

Ward et al., "Binding activities of a repertoire of single immunoglobulin variable domains secreted from *Escherichia coli,*" *Nature*, 1989, vol. 341, pp. 544-546.

Abdel-Hamid et al., "Flow-through immunofiltration assay system for rapid detection of *E. coli* O157:h7," *Biosens. Bioelectron.*, 1999, vol. 14, No. 3, pp. 309-316.

Cardullo, "Nonradioactive Fluorescence Resonance Energy Transfer," *Nonradioactive Labeling and Detection of Biomolecules*, C. Kessler, Editor, Springer-Verlag, New York, 1992, pp. 414-423.

Dabrowska et al., "The effect of bacteriophages T4 and HAP1 on in vitro melanoma migration," *BMC Microbiol.*, 2009, vol. 9, pp. 9-13.

Dictionary.com, "Microorganism," 2009, updated, //dictionary.reference.com/browse/microorganism, pp. 1-3.

Fines et al., "Activity of linezolid against Gram-positive cocci possessing genes conferrring resistance to protein synthesis inhibitors," *J. Antimicrob. Chemoth*., 2000, vol. 45, pp. 797-802.

Heid, et al., "Real time quantitative PCR," *Genome Research*, Oct. 1996, vol. 6, No. 10, pp. 986-994.

Mandeville et al., "Diagnostic and Therapeutic Applications of Lytic Phages," *Anal. Lett.*, 2003, vol. 36, No. 15, pp. 3241-3259.

Van De Plas et al., "Colloidal Gold as a Marker in Molecular Biology: The Use of Ultra-Small Gold Particles," *Nonradioactive Labeling and Detection of Biomolecules*, C. Kessler, Editor, Spring-Verlag, New York, 1992, pp. 116-126.

Wu et al., "A hairpin aptamer-based electrochemical biosensing platform for the sensitive detection of proteins," *Biomaterials*, 2009, vol. 30, pp. 2950-2955.

Goodridge et al., "Development and Characterization of a Fluorescent-Bacteriophage Assay for Detection of *Escherichia coli* O157:H7," *Applied and Environmental Microbiology*, Apr. 1999, vol. 65, No. 4, pp. 1397-1404.

Goodridge et al., "The use of a fluorescent bacteriophage assay for detection of *Escherichia coli* O157:H7 in inoculated ground beef and raw milk," *International Journal of Food Microbiology*, 1999, vol. 47, pp. 43-50.

Krishnamurthy et al., "Rapid Identification of Bacteria by Direct Matrix-assisted Laser Desorption/Ionization Mass Spectrometric Analysis of Whole Cells," *Rapid Communications in Mass Spectrometry*, 1966, vol. 10, pp. 1992-1996.

Cairns et al., "Quantitive Models of in Vitro Bacteriophage—Host Dynamics and Their Application to Phage Therapy," *PLos Pathogens*, 2009, vol. 5, No. 1, pp. 1-10.

In the US Patent and Trademark Office, U.S. Appl. No. 10/249,452, Non-Final Office Action dated Feb. 23, 2005, 12 pages; and corresponding response dated Aug. 26, 2005, 17 pages.

In the US Patent and Trademark Office, U.S. Appl. No. 10/249,452, Non-Final Office Action dated Feb. 7, 2006, 9 pages; and corresponding response dated Aug. 7, 2006, 7 pages, and supplemental response dated Aug. 30, 2006, 6 pages.

In the US Patent and Trademark Office, U.S. Appl. No. 10/823,294, Final Office Action dated Dec. 3, 2007, 14 pages; and corresponding response and RCE dated Mar. 3, 2008, 14 pages.

In the US Patent and Trademark Office, U.S. Appl. No. 10/893,294, Non-Final Office Action dated Apr. 25, 2008, 11 pages; and corresponding response dated Aug. 25, 2008, 5 pages.

In the US Patent and Trademark Office, U.S. Appl. No. 10/823,294, Non-Final office Action dated Jul. 23, 2007, 20 pages; and corresponding response dated Nov. 21, 2007, 24 pages.

In the US Patent and Trademark Office, U.S. Appl. No. 10/823,294, Non-Final Office Action dated Sep. 30, 2008, 8 pages; no response made.

Krueger et al., "The Kinetics of the Bacterium-Bacteriophage Reaction," The Journal of General Physiology, 1930, vol. 14, pp. 223-254.

* cited by examiner

METHOD FOR DETECTING CONCENTRATIONS OF A TARGET BACTERIUM THAT USES PHAGES TO INFECT TARGET BACTERIAL CELLS

CROSS REFERENCE TO RELATED APPLICATIONS

This application is a continuation of U.S. patent application No. 10/249,52, filed Apr. 10, 2003 and entitled "Method for Detecting Low Concentrations of a Target Bacterium That Uses Phages to Infect Target Bacterial Cells," now U.S. Pat. No. 7,166,425, which claims the benefit of U.S. Provisional Patent Application No. 60/319,184, filed Apr. 12, 2002 and entitled "Method for Detecting Low Concentrations of a Target Bacteria That Uses Phages to Infect Target Bacterial Cells"; the disclosures of which are hereby incorporated herein in their entireties.

FIELD OF THE INVENTION

The present invention relates to a method for detecting low concentrations of a target bacterium in a liquid mixture that uses bacteriophages to infect target bacterial cells.

BACKGROUND OF THE INVENTION

Standard microbiological methods have relied on substrate-based assays to test for the presence of specific organisms (Bordner, et al. 1978). These techniques offer very high levels of selectivity but are hindered by the requirement to first grow or cultivate pure cultures of the targeted organism, which can take 24 hours or longer. This time constraint severely limits the effectiveness to provide a rapid response to the presence of virulent strains of microorganisms.

Molecular biology techniques are quickly gaining acceptance as valuable alternatives to standard microbiological tests. In particular, serological methods have been widely employed to evaluate a host of matrices for targeted microorganisms (Kingsbury & Falkow 1985; Wyatt et al. 1992). These tests focus on using antibodies to first trap and then separate targeted organisms from other constituents in complicated biological mixtures. Once isolated, the captured organism can be concentrated and detected by a variety of different techniques that do not require cultivating the biological analyte.

One very popular approach, termed immunomagnetic separation (IMS), involves immobilizing antibodies to spherical, micro-sized paramagnetic beads and using the antibody-coated beads to trap targeted microorganisms from liquid media. The beads are easily manipulated under the influence of a magnetic field facilitating the retrieval and concentration of targeted organisms. Moreover, the small size and shape of the beads allow them to become evenly dispersed in the sample, accelerating the rate of interaction between bead and target. These favorable characteristics lead to reductions in assay time and help streamline the analytical procedure making it more applicable for higher sample throughput and automation.

Downstream detection methods previously used with IMS include ELISA (Cudjoe, et al. 1995), dot blot assay (Skjerve et al. 1990), electrochemiluminescence (Yu and Bruno 1996), and flow cytometry (Pyle, et al. 1999). Although these tests provide satisfactory results, they are laborious to perform and give binary responses (yes/no) that are highly susceptible to false-positive results due to cross-reactivity with non-target analytes. Recently reported is a rapid method for identifying specific bacteria from complex biological mixtures using IMS coupled to matrix-assisted laser desorption/ionization (MALDI) time-of-flight (TOF) mass spectrometry (MS)(Madonna et al. 2001). This approach allowed a variety of matrices to be evaluated for the presence of a *Salmonella* species within a total analysis time of 1 hour. Moreover, the developed procedure required little sample processing, was relatively easy to perform, and the molecular weight information obtained made it possible to discriminate between signals from the target bacteria and signals from cross-reacted constituents.

MALDI-TOF-MS is a proven technique for identifying whole cellular microorganisms (Holland et al (1996); van Barr 2000; Madonna et al. 2000). In principle, MALDI is a 'fingerprinting' technique where mass spectra featuring varying distributions of protein signals are generated. The signature profiles that are produced, due to inherent differences in microbial proteomes, make it possible to discriminate between organisms down to the strain level (Arnold and Reilly 1998). The MALDI-TOF technique coupled with IMS includes, in one embodiment, mixing immunomagnetic beads specific to the target bacteria with the liquid mixture that may contain the target bacteria for a short incubation period (e.g., 20 min). Any target bacteria captured by the beads are washed twice, re-suspended in deionized $H_2O$, and directly applied onto a MALDI sample probe. The target bacteria-bead complex is then overlaid with a micro-volume of matrix solution and dried at room temperature. Irradiation of the resulting crystalline mass with a high intensity laser promotes the liberation and ionization of intact cellular proteins that are subsequently detected by a TOF mass spectrometer. The resulting mass spectrum is then interrogated for definitive mass peaks that signify the presence of the target bacteria.

SUMMARY OF THE INVENTION

The invention is directed to a method for determining if a target bacterium is present in a liquid solution when the target bacterium is or may be present in a low concentration that is at or near the detection limit for a particular detection technology. As used herein, the term "target bacterium" refers to a specie of species of bacteria. In turn, the invention is applicable to situations in which it is desirable to determine whether a target bacterium (e.g., *E. coli*) is present in a liquid solution when the number of target bacterium per unit volume of solution (i.e., the concentration of the target bacterium) is or may be below the detection limit for a particular detection technology. In some instances, a plurality of target bacterium may be referred to as the target bacteria.

In one embodiment, the process comprises using a biological amplification procedure in which bacteriophages for the target bacterium are applied to the liquid solution. (Bacteriophages are viruses that infect bacteria and in the process produce many progeny. Structurally, the bacteriophage consists of a protein shell (capsid) that encapsulates the viral nucleic acid. The capsid is constructed from repeating copies of the same protein. Bacteriophages are able to infect specific bacterial cells and because of the multiplication of the genetic material, the cells eventually burst releasing millions of copies of the original phage.) The bacteriophages and any of the target bacterium present in the liquid solution are allowed to incubate. During the incubation period, the bacteriophages will multiply by infecting target bacterium present in the solution. More specifically, the bacteriophage replicates numerous copies of itself in an infected target bacterium. Eventually, the infected target bacterium lyses and the replicated or progeny bacteriophages are released into the liquid solution. The solution is then analyzed to determine if a biomarker for the bacteriophage is present, thereby indirectly indicating that the target bacterium is present in the liquid solution. Possible analysis techniques comprise mass spectrometry techniques, such as MALDI-MS and electro-spray ionization-MS techniques.

To assure that the detection of a biomarker for the bacteriophage indicates that the target bacterium is present in the liquid solution, a concentration of the bacteriophage is applied to the liquid solution that is below the detection limit for the biomarker for the bacteriophage for whatever analysis technique is employed. This assures that if the biomarker for the bacteriophage is detected by the analysis technique, the detectable concentration of the biomarker is attributable to the replication of the bacteriophage by the target bacterium present in the liquid solution. In certain situations, the use of such a concentration of bacteriophage has a multiplicity of infection ("MOI") (i.e., ratio of infecting bacteriophages to target bacterium) that is too low to rapidly produce a sufficient concentration of bacteriophages or biomarkers for the bacteriophage for detection.

Another embodiment of the process addresses this problem by adding a very high concentration of the bacteriophage to the liquid solution, thereby assuring a high MOI. In this case, the concentration of the bacteriophage added to the solution may exceed the detection limit of whatever analysis technique is employed to detect the bacteriophage or biomarker of the bacteriophage. Consequently, the process applies parent bacteriophage to the solution that can distinguished from any progeny bacteriophage resulting from the infection of target bacterium in the mixture. If the distinguishable progeny bacteriophage or a distinguishable biomarker of the progeny bacteriophage are present, this indicates that the target bacterium is present in the solution In one embodiment, the parent bacteriophage (i.e., the bacteriophage initially applied to the solution) are "tagged" so that whatever analysis technique is employed is inherently capable of distinguishing the parent bacteriophage or parent bacteriophage biomarkers from the progeny bacteriophage or biomarkers for the progency bacteriophage. For example, if a mass spectral analysis technique is employed, the parent bacteriophage are "tagged" with a substance that alters or shifts the mass spectrum of the parent bacteriophage relative to the progeny bacteriophage, which will not inherit the "tag" from the parent bacteriophage. For example, a biotinylated bacteriophage can be employed as a parent bacteriophage and will have a different mass spectrum than the progeny bacteriophage produced by the biotinylated bacteriophage infecting target bacterium present in the solution. Other "tags" can be employed for other types of analytical techniques.

In another embodiment, the parent bacteriophage possesses a characteristic that allows the parent bacteriophage to be separated from the progeny bacteriophage in the liquid solution prior to analysis, thereby assuring that most, if not all of the bacteriophages present in the liquid solution after separation are progeny bacteriophage resulting from the replication of the parent bacteriophage by target bacteria present in the liquid solution. In one embodiment, the parent bacteriophages initially applied to the liquid solution are biotinylated bacteriophages. Biotinylated bacteriophages are highly attracted to strepavidin. This attraction is exploited to separate the biotinylated bacteriophage from progeny bacteriophage resulting from replication of the biotinylated bacteriophage by target bacterium present in the mixture.

In one embodiment, the biotinylated bacteriophage attached to a strepavidin coated probe. Consequently, separation of the biotinylated bacteriophage from the liquid solution after the incubation period is accomplished by removing the probe from the liquid solution. In another embodiment, strepavidin-coated magnetic beads are applied to the liquid solution. The beads are used to pick up the biotinylated bacteriophage. The beads are then separated from the liquid solution using a magnet. In yet another, embodiment a strepavidin coated probe (e.g., a slide) is applied to the liquid solution after the incubation period. The biotinylated bacteriophage adhere to the probe and then the probe is separated from the liquid solution.

Yet a further embodiment of the invention recognizes that the liquid solution in which the target bacterium may be present is or may be a complex mixture that includes biological material that makes the detection of the bacteriophage or biomarker for the bacteriophage more difficult or reduces the reliability of the information provided by the detection technology employed. For instance, when a mass spectrometry detection methodology is employed, the complex mixture may produce a signal in which the biomarker associated with the bacteriophage is obscured or, stated differently, has a low signal-to-noise ratio. To address this possibility, the liquid solution is subject to a purification step in which target bacterium that are present in the liquid solution are separated from the remainder of the solution. In one embodiment, immuno-magnetic separation ("IMS") is utilized to separate target bacterium present in the liquid solution from the remainder of the solution. In one particular embodiment, magnetic beads are coated with an antibody for the target bacterium. The antibodies pick up the target bacterium present in the liquid mixture and then a magnet is used to separate the beads from the remainder of the liquid solution. The beads and any adhering target bacterium are then subjected to the biological amplification process and analysis. It should be appreciated this purification step also addresses the possibility that feral versions of the bacteriophage may be present in the liquid solution and that such versions could produce a false positive if the liquid solution was not subjected to a purification step.

If feral versions of the bacteriophage are not of concern, the purification step can be implemented after the biological amplification process. In this embodiment, the purification step involves separating the bacteriophages and the liquid solution, rather than separating the target bacterium and the liquid solution. In one embodiment, an IMS is used in which magnetic beads are coated with an antibody for the bacteriophage. The beads pick up the bacteriophages present in the solution and then a magnet is used to separate the beads from the remainder of the solution.

In another embodiment of the invention, the analysis step comprises using MS/MS analysis to determine if a biomarker for the target bacterium is present. The use of MS/MS analysis produces a highly reliable indication of the presence of a biomarker for a target bacterium. As a consequence, at least in some cases, the use of MS/MS analysis renders the need for a purification step unnecessary.

In yet another embodiment, the invention is directed to a process for detecting low concentrations of a target bacterium in complex mixtures. In one embodiment, the process comprises using an IMS procedure to isolate at least some of a target bacterium that may be present in a liquid mixture. The process further includes employing a biological amplification procedure in which a low titer or concentration of bacteriophages for the target bacterium are applied to at least some of the target bacterium that has been isolated by the IMS procedure. The mixture of bacteriophages and any of the target bacterium that has been isolated is allowed to incubate. If at least a certain concentration of the target bacterium is present, the bacteriophages will multiply during the incubation period such that a high titer or concentration of bacteriophages will be present in the mixture and detectable by MALDI-TOF-MS analysis. If no or only a small number of the target bacterium is present, there will be a low concentration of bacteriophages present in the mixture that will not be reasonably detectable by MALDI-TOF-MS analysis. Following incubation, a MALDI-TOF-MS analysis is performed on the incubated mixture of bacteriophages and target bacterium. The resulting mass spectrum is analyzed to determine if a protein that is associated with the bacteriophages is present. If the protein for the bacteriophage is detected, then it can be concluded that at least a low concentration of the target bacterium is present in the mixture.

It should also be appreciated that the method of the invention is capable of detecting low concentration of a target bacterium regardless of the manner in which the bacterium was grown or propogated.

DETAILED DESCRIPTION

Generally, the invention relates to the use of a bacteriophage to indirectly detect the presence of a target bacterium in a liquid solution where the concentration of the target bacterium is or is likely to be near or below the detection limit for the particular detection technology employed.

Bacteriophages are viruses that infect bacteria and in the process of infecting the bacteria produce many progeny. Structurally, the bacteriophage consists of a protein shell (capsid) that encapsulates the viral nucleic acid. The capsid is constructed from repeating copies of the same protein(s). Bacteriophages are able to infect specific bacterial cells and because of the multiplication of the number of progeny, the cells eventually burst releasing millions of copies of the original phage. This infection process has been utilized to serve as a biomarker amplification step for detecting low concentrations of target bacterial cells. For example, the capsid of the MS2 bacteriophage contains 180 copies of a 13 kDa protein. This particular virus specifically infects strains of *Escherichia coli* and is able to produce between 10,000 to 20,000 copies of itself within 40 min after attachment to the target bacterial cell. Essentially, one *E. coli* could be infected with MS2 resulting in the replication of the capsid protein(s) by a factor of $1.8 \times 10^6$.

The results from matrix assisted laser desorption ionization/mass spectrometry (MALDI/TOF) can be used to show the utility of the amplification step. MALDI-TOF-MS is a proven technique for identifying whole cellular microorganisms (Holland et al 1996; van Barr 2000; Madonna et al. 2000). In principle, MALDI is a 'fingerprinting' technique where mass spectra featuring varying distributions of protein signals are generated. The signature profiles are produced due to inherent differences in microbial proteomes that make it possible to discriminate between organisms down to the strain level (Arnold and Reilly 1998).

In an experiment where the protein MALDI signal from target bacterial cells was too weak for detection, the addition of low levels (too low to detect by MALDI) of the appropriate phage to the target bacterial cells after about thirty minutes produced a detectable protein MALDI signal attributable to the phage capsid protein. Bacteriophages specific for other bacterial species typically have capsid proteins of different molecular weight and therefore give a different MALDI signal. Therefore, the procedure is applicable to a multitude of different bacterial species. Other detection technologies, such as ion mobility spectrometry, optical spectroscopy, immuno techniques, chromatographic techniques and aptamer processes, are also feasible.

Generally, the process for detecting low concentrations of a target bacterium in a complex liquid mixture that contains or is likely to contain biological material other than the target bacterium comprises processing the mixture or a portion thereof to produce a liquid mixture, solution or sample for analysis that, if at least a certain concentration of the target bacterium is present in the mixture, a discernable signal or indication thereof is produced. It should be understood that the terms "liquid solution" and "liquid mixture" refer to the original solution or mixture that is the subject of the test and any liquid solutions or mixtures that, as a result of the application of the method, contain a portion of the original solution or mixture.

In one embodiment, the process comprises making a determination if a low concentration of a target bacterium is present in the liquid solution. This determination can be made by assuming that any of the target bacterium that are present in the liquid solution are present in a low concentration. Alternatively, an assay can be performed to determine if the target bacterium is present in a concentration that reliably exceeds the detection limit of whatever detection technology is being utilized. For instance, a mass spectrometry technique can be utilized. If the mass spectrometry technique provides a reliable signal indicative of the presence of the target bacterium in the liquid solution, no further steps needs to be taken. If, however, the mass spectrometry technique does not provide a reliable signal indicative of the presence of the target bacterium in the liquid solution, then it can be concluded that the target bacterium may be present in the liquid solution but in a concentration that below or near the detection limit of the mass spectrometry technique. In this case, further steps are taken to determine whether the target bacterium is present in the liquid solution in a concentration that is under the detection limit of the mass spectrometry technique.

The process involves a purification step that involves capturing the target bacterium that may be present in the mixture and separating any of the captured bacterium from other biological material that may be present in the mixture. By separating any of the captured target bacterium from other biological material that may be present in the mixture, the portion of the subsequently produced mass spectrum signal associated with other biological material present in the mixture is reduced. In one embodiment, an immunomagnetic separation (IMS) technique is used to capture and separate the target bacterium.

The process further comprises subjecting at least some of any of the captured and separated target bacterium to an amplification step in which the target bacterium are infected with a bacteriophage that is specific to the target bacterium. If there is at least a certain concentration of the target bacterium present, the bacteriophage will multiply to a point that a biomarker associated with the bacteriophage will be detectable using an analysis technique, such as MALDI/TOF-MS. In the case of MALDI/TOF-MS, a portion of the subsequently produced mass spectral signal indicative of the presence of the bacteriophage will be increased. If there is less than a particular concentration of the target bacterium present, the bacteriophage will not multiply sufficiently to be detectable in the mass spectrum produced using MALDI/TOF-MS. In essence, provided there is a least a certain concentration of the target bacterium present in the mixture, the purification and amplification steps serve to increase the signal-to-noise ratio for the portion of the subsequently produced mass spectrum that is associated with the bacteriophage.

After amplification, at least a portion of the amplified mixture is subjected to analysis to determine if a biomarker for the target bacterium is present. For example, MALDI/TOF-MS analysis can be used to produce a mass spectrum. The mass spectrum is analyzed to determine if one or more biomarkers for the bacteriophage are present. If such biomarkers are present, this is an indirect indication that at least a certain concentration of the target bacterium was present in the originally sampled mixture.

It should be appreciated that the need for the purification step may not be necessary in situations in which the portion of the signal associated with other biological materials can be filtered, eliminated or otherwise ignored and/or in situations in which the amplification step has a gain such that the portion of the mass spectrum associated with the bacteriophage is likely to exceed any background signal associated with other biological materials and/or situations in which a false positive is considered to be remote. Further, it should also be appreciated that one of the other biological materials that can make it difficult to determine if the biomarker for the bacteriophage is present is a wild version of the bacteriophage that is present in the liquid solution that is being tested. The purification step addresses the presence of a wild bacteriophage.

If the presence or possible presence of a wild bacteriophage in the solution or mixture being tested is not a concern, it is also possible to perform a purification step after the amplification step. However, in this case, the bacteriophage is separated from the remainder of the liquid solution. The previously noted IMS technique can be employed. However, the magnetic bead is coated with an antibody for the bacteriophage, rather than an antibody for the target bacterium.

Figure 1:
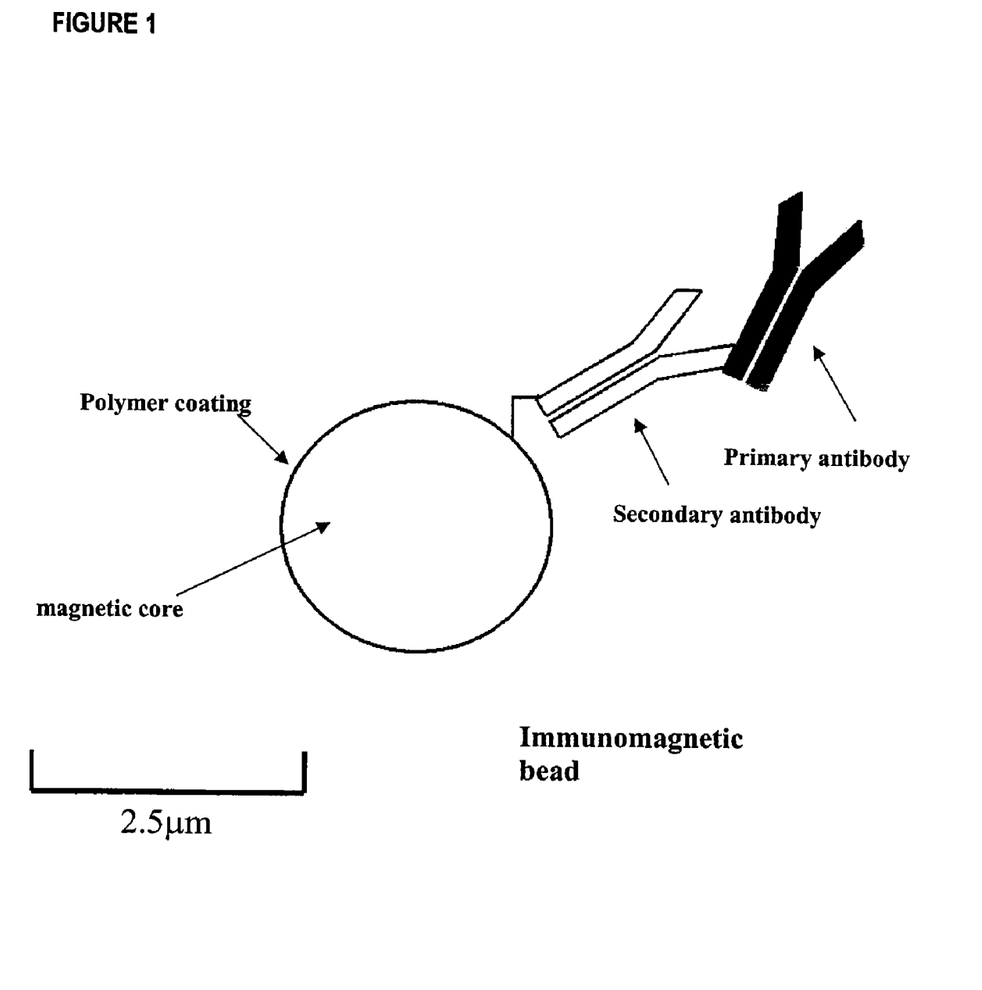
FIG. 1 depicts, for one embodiment of the invention, an immunomagnetic bead that is used to isolate the target microorganism (antibodies not drawn to scale)

It is also possible in certain cases to eliminate the need for a purification step by utilizing a highly specific analysis technique, such as MS/MS, in which the biomarker for the bacteriophage is so highly specific to the bacteriophage that there is little likelihood of a false positive. Currently, the use of MS/MS is limited to capsid proteins that are less than 7000 Da.W With reference to FIG. 1, the immunomagnetic separation (IMS) technique for capturing the target bacterium in a mixture and separating any captured target bacterium from other biological material in the mixture is described. Microsize beads are constructed from an iron oxide core coated with a polymeric surface. Secondary antibodies raised against the Fc region of the primary antibodies are covalently attached via a linker to the polymer surface. The primary antibody (raised against a targeted microorganism) is attached to the beads by strong noncovalent interactions with the secondary antibody, which holds the primary antibody in the proper orientation for reaction with the targeted antigen.

Figure 2:
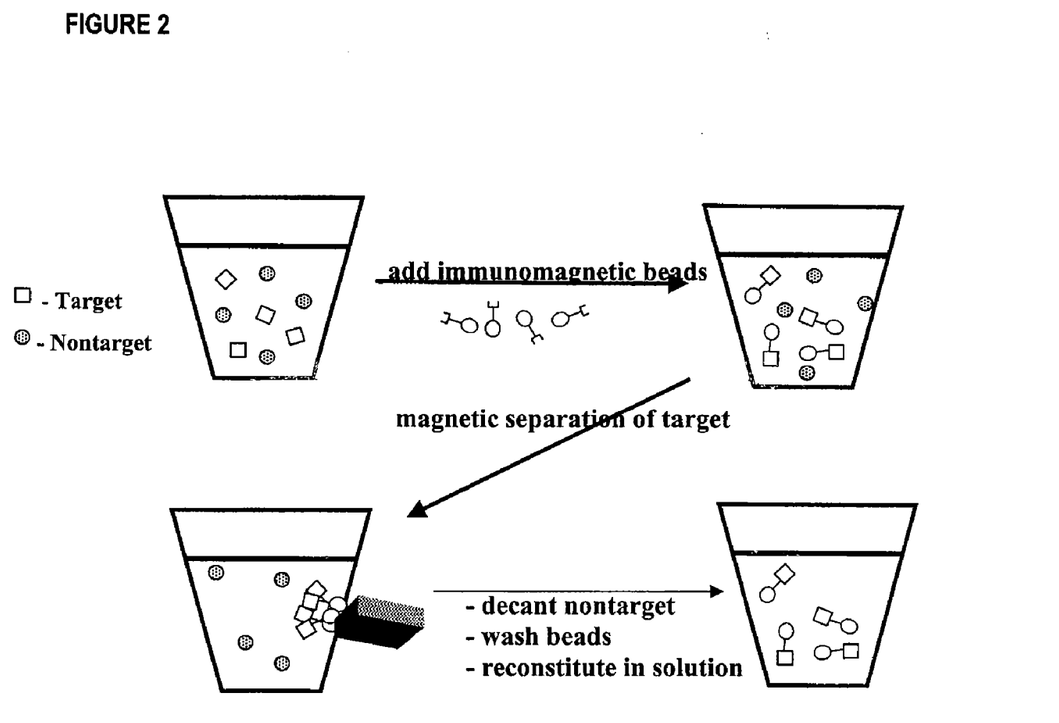
FIG. 2 is a schematic representation of the immunomagnetic purification step used to isolate a target antigen (*Escherichia coli*) in one embodiment of the invention.

With reference to FIG. 2, the immunomagnetic beads are added to the bacterial or biological mixture that is the subject of the analysis and incubated for 20 minutes at room temperature. The beads are then isolated to the side of the reaction tube using a magnet. This process allows the extraneous (non-targeted) material to be removed by aspiration. At this stage, the beads can be washed several times prior to resuspending them in PBS.

Figure 3:
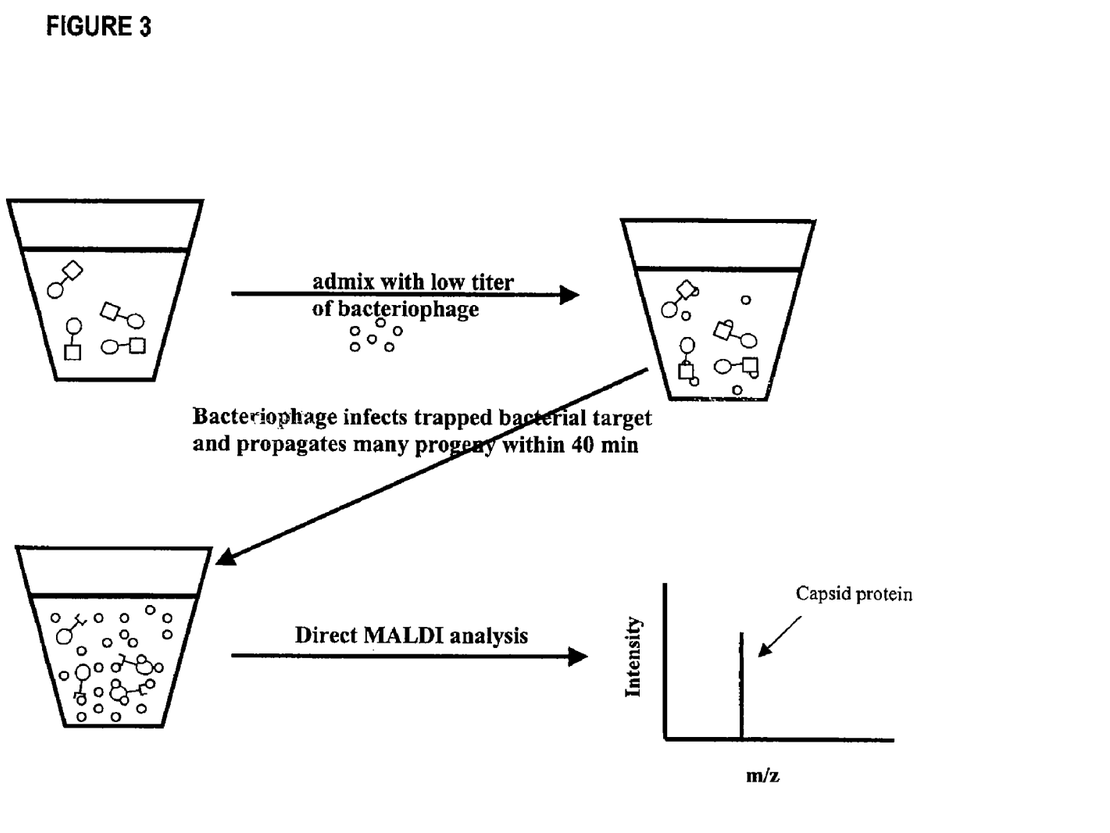
FIG. 3 is a schematic representation of the bacteriophage amplification step for one embodiment of the invention.

With reference to FIG. 3, the bead-bacterial target complex is admixed with a low titer suspension of bacteriophage specific to the targeted bacterium. The titer is held low so that the mass spectrometry signal from the virus is non-detectable. After a 40-minute incubation, the bacteriophage have completed a propagation cycle of attachment, insertion, self-assembly, and cell lysis resulting in the production of many progeny that are released into the reaction milieu. The milieu is then analyzed to determine if a biomarker for the bacteriophage is present that indirectly indicates that the target bacterium was present. For instance, the milieu can be analyzed by MALDI-TOF-MS using a sandwich sample preparation technique with a ferulic acid matrix. Other MALDI matrices known in the art are also feasible. The resulting mass spectrum shows the presence of the bacteriophage capsid protein, which would not have been present if the target bacterium was not also present.

An IMS technique for capturing target bacterium in a mixture and separating any captured target bacterium from other biological material in the mixture and subsequent MALDI-TOF/MS analysis are described in U.S. patent application Ser. No. 10/063,346, entitled "Method for Determining if a Type of Bacteria is Present in a Mixture," filed on Apr. 12, 2002, which is incorporated herein, in its entirety, by reference.

EXAMPLE

Figure 4:
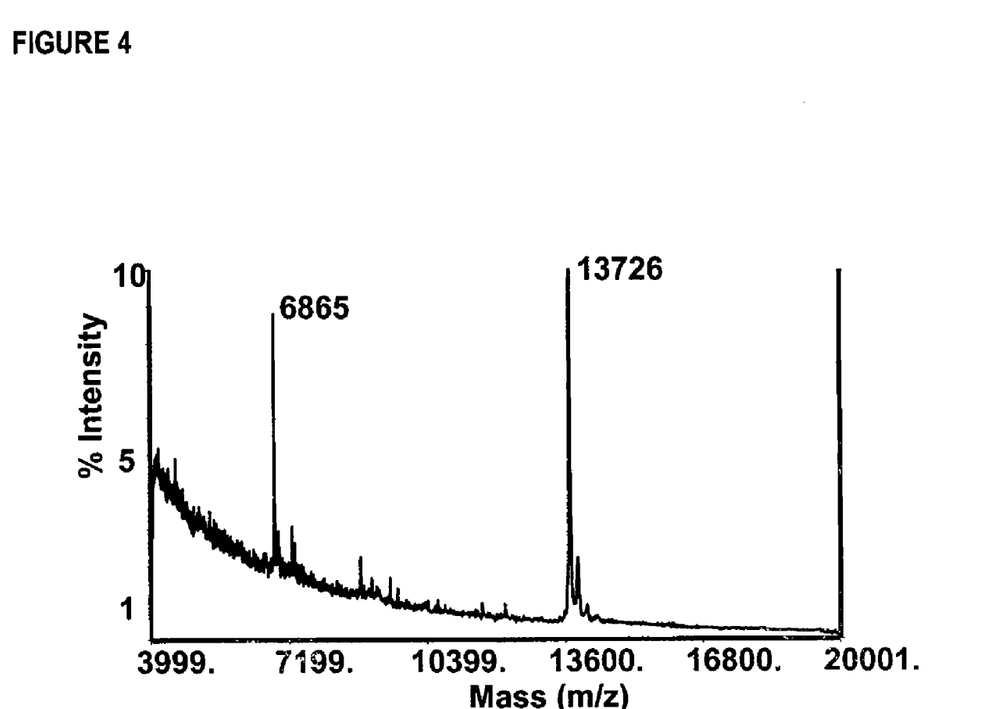
FIG. 4 shows a typical MALDI-TOF mass spectrum obtained from a high titer sample of MS2 in PBS.

As described hereinafter, an embodiment of the method has been used to reduce the detection limit for $E.\ coli$ to less than $5.0\times10^4$ cells $mL^{-1}$. The method used immunomagnetic beads coated with antibodies against $E.\ coli$, hereinafter referred to as the target-bead complex, to isolate the bacterium from solution. The target-bead complex was then resuspended in a solution containing MS2, a bacteriophage that is specific for $E.\ coli$. The MS2 bacteriophage concentration was adjusted so that the ion signal from the capsid protein of the MS2 bacteriophage was below the detection limit of the mass spectrometer. After a 40-minute incubation period, an aliquot of the solution was removed and analyzed by the on-probe MALDI-TOF-MS procedure for the 13 kDa capsid protein. The $[M+H]^+$ (m/z 13,726) and $[M+2H]^{+2}$ (m/z 6865) ion signals for the MS2 capsid protein were detected (FIG. 4).

Figure 5:
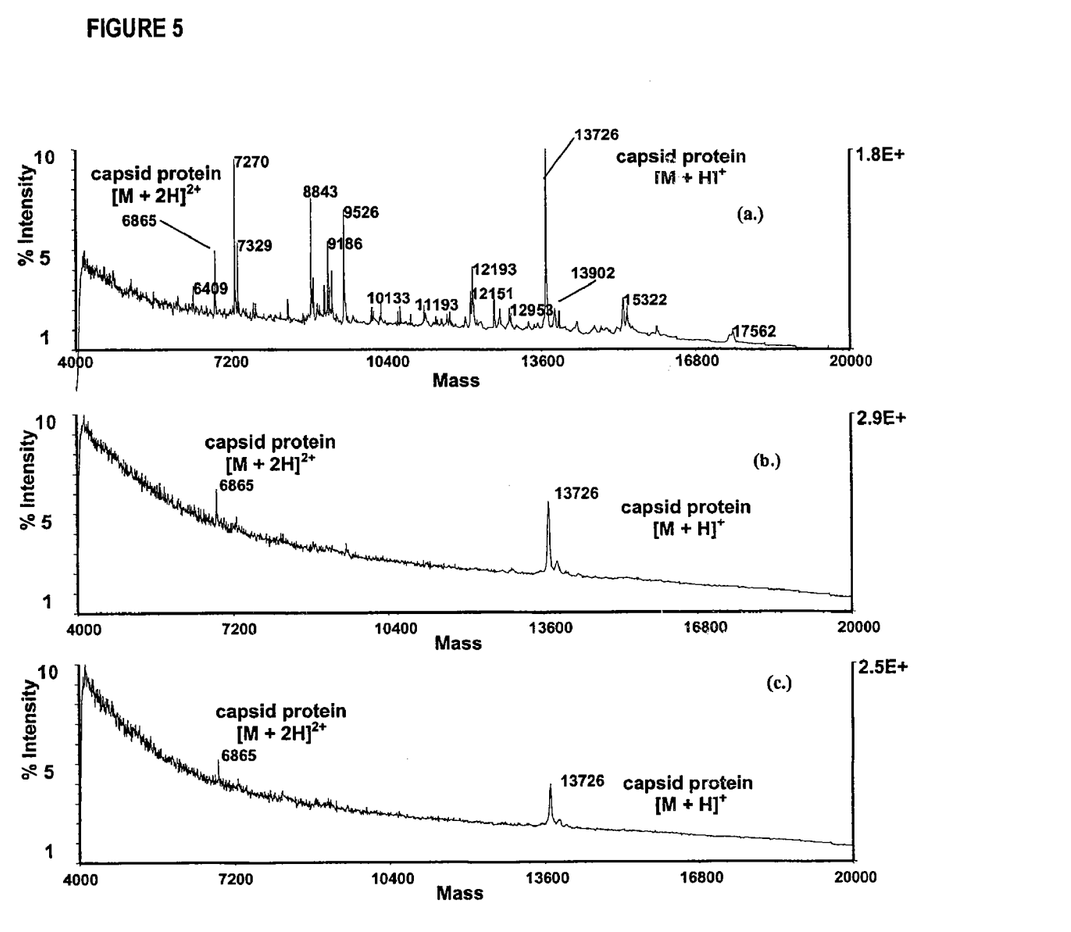
FIGS. 5A-5C illustrate how an embodiment of the invention was able detect a biomarker of the bacteriophage indicative of presence of *E. coli* for decreasing concentrations of *E. coli*.

With reference to FIG. 5A, application of the process to a mixture that contains a concentration of $5.0\times10^6$ $E.\ coli$ cells $mL^{-1}$ yields a mass spectrum with protein signals for both $E.\ coli$ and the MS2 bacteriophage. The process was repeated for decreasing concentrations of $E.\ coli$. Specifically, with reference to FIG. 5B, the process was repeated for a concentration of ~$5.0\times10^5$ $E.\ coli$ cells $mL^{-1}$. In this case, the mass spectrum fails to definitively show any protein signals for the $E.\ coli$ cells, but does show the protein signals for the MS2 bacteriophage capsid protein. With reference to FIG. 5C, the process was repeated for an $E.\ coli$ concentration of ~$5.0\times10^4$ cells $mL^{-1}$. In this case, the mass spectrum fails to definitively show any protein signals for the $E.\ coli$ cells but still show protein signals for the MS2 bacteriophage capsid protein. These results indicate that $E.\ coli$ was trapped by the immunomagnetic beads and then infected by the MS2 virus, which was able to multiply and increase the concentration of the capsid protein to a detectable level. Presently, target bacterium concentrations of as low as ~$1.0 \times 10^3$ cells mL$^{-1}$ have been indirectly detected using this process.

The following describes various aspects of the embodiment of the method implemented with respect to the example of the detection of *E. coli*.

E. coli Preparation

The *E. coli* bacteria were grown in trypticase soy broth (TSB) (Difco, Detroit, Mich.) with incubation at 37° C. using standard microbial methods.

Bacteriophage Propagation

Bacteriophage propagation was performed in accordance to the Adams agar-overlay method as described in M. H. Adams' Bacteriophages (Interscience Publishers, Inc., New York, 1959). Briefly, a soft-agar/host covering was prepared by overlaying agar plates (trypticase soy agar, Difco) with a 2.5 mL of melted 0.5% agar (same medium), which contained two drops of a 20 hr host in TSB. The soft-agar covering was allowed to harden before the addition of a 0.5 mL overlay of a concentrated suspension of MS2, prepared by re-hydrating freeze-dried MS2 in TSB. After 24 hours, the soft agar was scraped off the surface of the agar plates and centrifuged (1000 G) for 25 min to sediment the cellular debris and agar. The supernatant was conserved, passed through 0.22 μm Millipore filters, and stored by refrigeration at 4-8° C.

Immunomagnetic Bead Preparation R

Rabbit anti-*E. coli* IgG antibodies (Cortex Biochem, San Leandro, Calif.) were attached to the immunomagnetic beads (MagaBeads, Goat anti-Rabbit IgG F(c), Cortex Biochem) using the manufacturer's suggested protocol.

Immunomagnetic separation (IMS) *E. coli* E

*Escherichia coli* were isolated from aqueous suspensions by affinity capture using the immunomagnetic beads. Suspensions of bacteria were prepared in 1.5 mL microcentrifuge tubes (Brinkmann Instruments, Inc., Westbury, N.Y.) by combining 100 μL of broth media with 900 μL of phosphate buffer saline (PBS, 0.01 M Na$_2$ HPO$_4$, 0.15M NaCl titrated to pH 7.35 with HCl). Cell concentrations were determined using a Petroff-Hauser counting chamber (Hauser Scientific, Horsham, Pa.).

The immunomagnetic separation (IMS) procedure developed in this investigation involved the following steps: In the first step, a 30 μL aliquot of the immunomagnetic beads were added to the bacterial sample solution and incubated for 20 minutes at room temperature with continuous shaking. The second step involved concentrating the beads to the side of the sample tube using a magnetic particle concentrator (Dynal, Lake Success, N.Y.) and removing the supernatant using a 1 mL pipette. In the third step, the magnet was removed and the beads were re-suspended in 1 mL of fresh PBS with vigorous shaking for 20 sec to wash away any nonspecifically adhering components. The bead suspension was then transferred to a new tube and steps 2 and 3 repeated one more time. In the fourth and final step, the beads were isolated with the magnet followed by decanting the buffer wash to waste and re-suspending the beads in 500 μL of deionized water. Subsequently, the bead-*E. coli* complexes were admixed with a low titer (below the detection limit of the mass spectrometer) of the MS2 bacteriophage and incubated at room temperature with gentle shaking for 40 minutes. An aliquot of the suspension was then removed and analyzed for the MS2 capsid protein using a sandwich sample preparation with a ferulic acid matrix (12.5 mg of ferulic acid in 1 mL of 17% formic acid: 33% acetonitrile: 50% deionized H$_2$O).

MALDI-TOF MS

All mass spectra were generated on a Voyager-DE STR+ (AB Applied Biosystems, Framingham, Mass.) MALDI-TOF mass spectrometer, operating in the positive linear mode. The following parameters were used: accelerating voltage 25 kV, grid voltage 92% of accelerating voltage, extraction delay time of 350 nsec, and low mass ion gate set to 4 kDa. The laser intensity (N$_2$, 337 nm) was set just above the ion generation threshold and pulsed every 300 ns. Mass spectra were acquired from each sample by accumulating 100 laser shots from five different sample spots (final spectrum=average of 5×100 laser shots).

It should be appreciated that to assure that the detection of a biomarker for the bacteriophage indicates that the target bacterium is present in the liquid solution, a concentration of "parent" bacteriophage is applied to the liquid solution that is below the detection limit for the bacteriophage or biomarker for the bacteriophage for whatever analysis technique is employed. This assures that if the bacteriophage or the biomarker for the bacteriophage is detected by the analysis technique, the detectable concentration of the bacteriophage or biomarker is attributable to progeny bacteriophage, i.e., bacteriophage resulting from the replication of the bacteriophage by the target bacterium present in the liquid solution. In certain situations, the use of such a concentration of "parent" bacteriophage has a multiplicity of infection ("MOI") (i.e., the ratio of the number of parent bacteriophage to the number of target bacterium) that is too low to produce a sufficient concentration of bacteriophages or biomarkers for the bacteriophage for detection.

To overcome the drawbacks associated with a low MOI, a sufficiently high concentration of "parent" bacteriophage is added to the liquid solution. In this case, the concentration of the "parent" bacteriophage added to the solution may exceed the detection limit of whatever analysis technique is employed to detect the bacteriophage or biomarker of the bacteriophage. Consequently, analysis of a liquid solution treated in this manner could detect the "parent" bacteriophages that were added to the solution, rather than the progeny bacteriophage resulting from replication by the target bacteria.

Consequently, another embodiment of the process applies a concentration of "parent" bacteriophage to the solution that is capable of being distinguished from any progeny bacteriophage. In one embodiment, the parent bacteriophage (i.e., the bacteriophage initially applied to the solution) are "tagged" so that whatever analysis technique is employed is inherently capable of distinguishing the parent bacteriophage or parent bacteriophage biomarkers from the progeny bacteriophage or biomarkers for the progeny bacteriophage. For example, if a mass spectral analysis technique is employed, the parent bacteriophage are "tagged" with a substance that alters or shifts the mass spectrum of the parent bacteriophage relative to the progeny bacteriophage, which will not inherit the "tag" from the parent bacteriophage. For example, a biotinylated bacteriophage is employed as a parent bacteriophage and has a different mass spectrum than the progeny bacteriophage produced by the biotinylated bacteriophage infecting target bacterium present in the solution. Other "tags" can be employed for other types of analytical techniques.

In another embodiment, the parent bacteriophage possesses a characteristic that allows the parent bacteriophage to be separated from any of the progeny bacteriophage in the liquid solution prior to analysis, thereby assuring that most, if not all of the bacteriophage present in the liquid solution after separation are progeny bacteriophage resulting from the replication of the parent bacteriophage by target bacteria present in the liquid solution. In one embodiment, biotinylated bacteriophage are initially applied to the liquid solution. Biotinylated bacteriophage are highly attracted to strepavidin. Consequently, to separate the biotinylated bacteriophage from the liquid solution a strepavidin probe is utilized. In one embodiment, the biotinylated bacteriophage are attached to a strepavidin coated probe and the probe is placed in the liquid solution. In this case, separation of the biotinylated bacteriophage from the liquid solution after the incubation period is accomplished by removing the probe from the liquid solution. In another embodiment, strepavidin-coated magnetic beads are applied to the liquid solution. The biotinylated bacteriophages are attached to the strepavidin-coated magnetic beads prior to the application of the beads to the solution. Alternatively, the beads are used to pick up biotinylated bacteriophages that were previously added to the solution and then separated from the liquid solution using a magnet. In yet another, embodiment a strepavidin coated probe (e.g., a slide) is applied to the liquid solution after the incubation period. The biotinylated bacteriophages adhere to the probe and then the probe is separated from the liquid solution. Regardless of the manner in which the biotinylated bacteriophages are separated from the liquid mixture, at least a portion of the solution is then subjected to analysis to determine if the bacteriophage or a biomarker for the bacteriophage is present, which indirectly indicates that the target bacteria was present in the solution.

The invention claimed is:

1. A method for determining if a target bacterium is present in a liquid solution when the target bacterium is below the detection limit for a particular detection technology comprising:

combining a first quantity of a bacteriophage with a liquid suspension comprising a first quantity of target bacteria to infect at least some of said target bacteria and multiply the number of bacteriophage in said liquid solution, wherein each of said first quantity of target bacteria and the first quantity of bacteriophage is at a concentration below the detection limit for said detection technology; and analyzing at least a portion of said liquid suspension by said detection technology to determine if a biomarker for said bacteriophage is present in order to determine the presence of said target bacterium in said liquid solution.

2. A method, as claimed in claim 1, wherein: said step of analyzing comprises performing an immuno analysis.

3. A method, as claimed in claim 1 further comprising separating said target bacterium from said liquid suspension before said combining step.

4. A method, as claimed in claim 3, wherein: said step of separating comprises using immuno-magnet beads coated with antibodies for said target bacterium.

\* \* \* \* \*